United States Patent [19]

Grollier et al.

[11] 4,348,202

[45] * Sep. 7, 1982

[54] HAIR DYE OR BLEACH SUPPORTS

[75] Inventors: Jean-Francois Grollier; Chantal Fourcadier, both of Paris, France

[73] Assignee: L'Oreal, Paris, France

[*] Notice: The portion of the term of this patent subsequent to May 6, 1997, has been disclaimed.

[21] Appl. No.: 158,271

[22] Filed: Jun. 10, 1980

[30] Foreign Application Priority Data

| | | | |
|---|---|---|---|
| Jun. 15, 1978 | [FR] | France | 78 17899 |
| Jun. 14, 1979 | [BE] | Belgium | 195.741 |
| Jun. 14, 1979 | [IT] | Italy | 68281 A/79 |
| Jun. 14, 1979 | [CH] | Switzerland | 5592/79 |
| Jun. 15, 1979 | [CA] | Canada | 329838 |
| Jun. 15, 1979 | [DE] | Fed. Rep. of Germany | 2924230 |
| Jun. 15, 1979 | [JP] | Japan | 54-75560 |
| Jun. 15, 1979 | [GB] | United Kingdom | 7920878 |
| Dec. 13, 1979 | [FR] | France | 79 30586 |

[51] Int. Cl.$^3$ .............................................. A61K 7/06
[52] U.S. Cl. ........................................ 8/406; 424/70; 424/DIG. 3
[58] Field of Search .............. 8/405, 425, 435, 127.51, 8/406; 424/DIG. 2, 70

[56] References Cited

U.S. PATENT DOCUMENTS

| | | | |
|---|---|---|---|
| 3,678,157 | 7/1972 | Kalopissis et al. | 8/127.51 |
| 3,882,114 | 5/1975 | Kalopissis et al. | 8/127.51 |
| 4,157,388 | 6/1979 | Christiansen | 8/127.51 |
| 4,166,845 | 9/1979 | Hansen et al. | 424/DIG. 2 |
| 4,201,766 | 5/1980 | Grollier et al. | 424/DIG. 2 |

Primary Examiner—Ethel G. Love
Attorney, Agent, or Firm—Cushman, Darby & Cushman

[57] ABSTRACT

This invention has for its object the use of certain quaternized polymers as cosmetic agents in certain particular cosmetic compositions.

47 Claims, No Drawings

HAIR DYE OR BLEACH SUPPORTS

This application is a continuation-in-part of application Ser. No. 048,585, filed June 13, 1979, now abandoned.

This invention more precisely has for its object cosmetic compositions for the hair wherein they comprise at least a polymer whose macrochain contains groups of formula I:

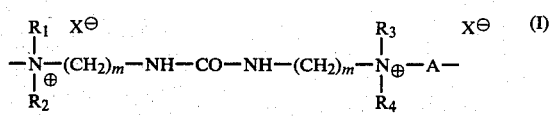

wherein $R_1$, $R_2$, $R_3$ and $R_4$, equal or different represents a saturated or unsaturated, substituted or unsubstituted aliphatic radical, a saturated or unsaturated, substituted or unsubstituted alicyclic radical, or a substituted or unsubstituted arylaliphatic radical, or else two residues $R_1$ and $R_2$ (or $R_3$ and $R_4$) attached to the same nitrogen atom constitute with it a ring that can contain a second heteroatom other than nitrogen, A represents a substituted or unsubstituted, branched or linear alkylene or alkenylene group, possibly comprising one or more heteroatoms or one or more arylene groups, $X^-$ is an inorganic or organic acid anion and m is a number equal to 2 or 3, and wherein they contain ingredients making it possible to exhibit them in the form of a dye or bleach support or in the form of a permanent composition, or a pre- or postpermanent lotion.

Of the polymers that correspond to this definition, there will be cited particularly those for which $R_1$, $R_2$, $R_3$ and $R_4$, equal or different, represent an alkyl or hydroxyalkyl group comprising from 1 to 20 carbon atoms, a cycloalkylalkyl radical having less than 20 carbon atoms, a cycloalkyl radical with 5 or 6 groups, an aralkyl radical such as a phenylalkyl radical whose alkyl group preferably comprises 1 to 3 carbon atoms; or else two residues $R_1$ and $R_2$ (or $R_3$ and $R_4$) attached to the same nitrogen atom, together represent a polymethylene radical having 2 to 6 carbon atoms, so as to form with said nitrogen atom a ring that can comprise a second heteroatom, for example, oxygen or sulfur; A represents a linear or branched alkylene or alkenylene group, possibly substituted by one or more groups such as —OH or =O, and possibly interrupted by one or more heteroatoms or oxygen, sulfur or nitrogen and/or by one or more phenylene groups, and having 2 to 18 carbon atoms, and in particular A can represent an ortho-, meta- or para-xylylene or a radical of the formula:

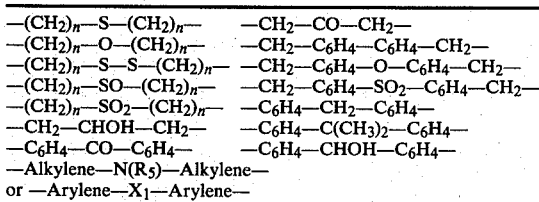

$X_1$ being selected from the group consisting of —O—, —S—, —S—S—, —SO—, —SO$_2$— and —N(R$_5$)—, $R_5$ being selected from alkyl, cycloalkyl and aralkyl having up to 20 carbon atoms, the Alkylene and Arylene groupings having up to 20 carbon atoms, n being an integer equal to 2 or 3;

and $X^-$ is a halide (bromide, chloride or iodide) ion or an anion derived from other inorganic acids such as phosphoric acid or sulfuric acid, or again an anion derived from an organic sulfonic (particularly paratoluene sulfonic) or carboxylic acid.

It should be noted that the invention extends to the use of polymers for which the A groups and the couples ($R_1$, $R_2$) or ($R_3$, $R_4$) have several different values in the same polymer.

Although the invention is not limited to the use of polymers having a determined degree of polymerization, it can be noted that the polymers that can be used according to the invention generally have a molecular weight between about 1,500 and 50,000.

Of the polymers having quaternized nitrogen atoms such as defined above there will be cited particularly the polymers whose groups answer to formula I above, and in particular those for which $R_1=R_2=R_3=R_4=CH_3$ or $C_2H_5$ and those for which A represents:

—(CH$_2$)$_n$—O—(CH$_2$)$_n$—, n being defined as above,
—CH$_2$—C$_6$H$_4$—CH$_2$—,    —CH$_2$—CHOH—CH$_2$—,
—(CH$_2$)$_p$—p being an integer that can vary from 2 to 18, and —(CH$_2$)$_{n1}$—CH=CH—(CH$_2$)$_{n2}$—, $n_1$ and $n_2$ being integers, including zero, whose sum is at most equal to 16.

Of the preferred polymers, there is particularly mentioned that those that correspond to formula 1 with
$R_1=R_2=R_3=R_4=CH_3$,
m=3,
X=Cl, and
A=—CH$_2$CH$_2$—O—CH$_2$—CH$_2$—, (polymer P$_1$)
A=—CH$_2$—CHOH—CH$_2$—, (polymer P$_2$)
A=—CH$_2$—C$_6$H$_4$—CH$_2$, (polymer P$_3$)
A=—CH$_2$—CH=CH—CH$_2$—, (polymer P$_4$)
A=(CH$_2$)$_6$, (polymer P$_5$)
and those of formula I with
$R_1=R_2=R_3=R_4=C_2H_5$,
m=3
X=Cl and
A=—(CH$_2$)$_6$ (Polymer P$_6$)
A=—CH$_2$—CHOH—CH$_2$—(Polymer P$_7$)
A=—CH$_2$—CH=CH—CH$_2$ (Polymer P$_8$)

The polymers used according to the present invention can also be copolymers containing in addition groups of formula II

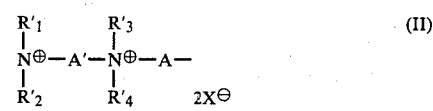

wherein $R'_1$, $R'_2$, $R'_3$ and $R'_4$ are defined at $R_1$, $R_2$, $R_3$ and $R_4$, A' is a linear or branched alkylene group or substituted or unsubstituted arylene, able to contain up to 20 carbon atoms, and A is defined as above.

Of these polymers there will be particularly cited polymers P$_9$ to P$_{14}$ whose composition is indicated below in the experimental part.

The polymers mentioned above can be prepared particularly according to a process similar to those described in French patent application No 75 15162.

The cosmetic hair composition of this application contain ingredients and adjuvants that make it possible to offer them in the form of dye or bleach supports or compositions or in the form of permanent compositions.

It is known that in the present art of hair dyeing or bleaching, dye or bleach supports are used that make it possible to offer the composition in the form of cream or in the form of gel or liquid gelable by dilution.

Generally, creams are obtained from fatty acid soaps with $C_{12}$ to $C_{20}$, or from fatty alcohols in the presence of anionic or nonionic emulsifiers.

The soaps can be made from natural or synthetic fatty acids having 12 to 20 carbon atoms such as: lauric acid, myristic acid, palmitic acid, oleic acid, stearic acid, hydroxystearic acid, arachic acid, ricinoleic acid, lanolinic acid, phenylstearic acid, linoleic acid, with concentrations between 1 and 60% and preferably between 5 and 30% (before dilution).

The alkalizing agents used to form the soaps can be particularly soda, potash, ammonia, monoethanolamine, diethanolamine, triethanolamine, mono and diisopropanolamine, N-ethylmorpholine, 2-amino-1-butanol, 2-amino-2-methyl-1-propanol or their mixtures.

The creams can also be formulated from natural or synthetic alcohols having between 12 and 20 carbon atoms in mixture with the emulsifiers.

Of the fatty acids, there can be cited in particular alcohols derived from copra fatty acids, myristic alcohol, cetyl alcohol, stearyl alcohol, arachidyl alcohol, isostearyl alcohol, hydroxystearyl alcohol, oleic alcohol, ricinoleic alcohol, in concentrations generally between 1% and 60% and preferably between 5% and 30%.

The emulsifiers that can be used in the compositions in cream form can be oxyethylenated or polyglycerolated natural or synthetic fatty alcohols with $C_{10}$–$C_{20}$ as, for example, polyoxyethylenated oleic alcohol comprising from 10 to 30 moles of ethylene oxide, oxyethylenated cetyl alcohol comprising from 6 to 10 moles of ethylene oxide, cetylstearyl alcohol oxyethylenated with 10 moles of ethylene oxide, oleocetyl alcohol with 30 moles of ethylene oxide, stearyl alcohol with 10, 15 or 20 moles of ethylene oxide, oleic alcohol polyglycerolated with 4 moles of glycerol and synthetic fatty alcohols comprising between 9 and 20 carbon atoms polyoxyethylenated with 5 to 30 moles of ethylene oxide.

These nonionic emulsifiers are present in concentrations generally between 1% and 60% and preferably from 5% to 30% by weight.

Other emulsifiers can be alkyl sulfates that have or have not been oxyethylenated, such as sodium lauryl sulfate, ammonium lauryl sulfate, sodium cetylstearylsulfate, triethanolamine cetylstearylsulfate, monoethanolamine or triethanolamine lauryl sulfate, oxyethylenated sodium lauryl ether sulfate comprising, for example, 2.2 moles of ethylene oxide, oxyethylenated monoethanolamine lauryl ether sulfate comprising, for example, 2.2 moles of ethylene oxide.

These constituents are present in concentrations generally between 1% and 60% and preferably between 3% and 15% by weight.

These creams can further contain various usual adjuvants such as fatty amide.

Of the fatty amides there are preferably used mono or di-ethanolamides, copra derived acids, lauric acid or oleic acid, in concentrations generally between 0 and 15% by weight.

They can also contain sequestering agents such as ethylenediaminetetraacetic acid or its salts, thickeners, perfumes, etc.

Generally, gelable liquids are obtained either from oxyethylenated or polyglycerolated nonionic compounds and solvent or from liquid fatty acid soaps, such as those of oleic, linoleic, ricinoleic acids or isostearic acid and solvents.

The alkalizing agents used to form the soaps can be an alkaline base or an amine, particularly soda, potash, ammonia, monoethanolamine, diethanolamine, triethanolamine, mono- or di-isopropanolamine, N-ethylmorpholine, 2-amino-1-butanol, 2-amino-2-methyl-1-propanol or their mixture.

Of the oxyethylenated nonionic compounds there can be cited natural or synthetic liquid fatty alcohols such as oleic alcohol with 4 and 10 moles of ethylene oxide, synthetic fatty alcohol with $C_{10}$–$C_{20}$ with 4 and 6 moles of ethylene oxide, synthetic fatty alcohols with $C_9$–$C_{15}$ with 2, 6 and 9 moles of ethylene oxide.

Of the oxyethylenated nonionic compounds there can be cited in particular nonylphenol polyether with 4 moles of ethylene oxide and nonylphenol polyether with 9 moles of ethylene oxide.

These constituents are present in concentrations between 5 and 60% by weight and preferably between 5% and 40% by weight.

Of the polyglycerolated nonionic compounds there can be cited in particular oleic alcohol with 2 moles of glycerol and glycerolated oleic alcohol with 4 moles of glycerol.

These constituents are present in concentrations generally between 5% and 60% by weight and preferably between 5% and 40% by weight.

The solvents used can be lower aliphatic alcohols such as ethyl alcohol, propyl alcohol or isopropyl alcohol, glycols such as propylene glycol, methyl glycol, ethyl glycol, and butyl glycol, diethylene glycol, dipropylene glycol, hexylene glycol, or diethylene glycol monoethyl ether.

These solvents or their mixtures are generally used in concentrations (before dilution) of 2 to 20% and preferably 5 to 15% by weight.

The gelable composition can further contain various usual adjuvants.

These adjuvants can be fatty amides, natural or synthetic fatty alcohols, oxyethylenated or not alkaline alkyl sulfates, preservative agents, sequestering agents and perfumes.

Of the fatty amides there can be cited in particular oleic or lauric diethanolamide, copra mono or diethanolamide.

These amides are generally used in concentrations (before dilution) of 0.5 to 15% and preferably 1 to 10% by weight.

Of the natural or synthetic alcohols there can be cited in particular oleic lauric, octyldodecyl, hexyldodecyl, isostearyl, ricinoleyl, linoleyl alcohols.

These alcohols are generally used in concentrations (before dilution) of 1 to 25% and preferably 5 to 15% by weight.

Of the alkaline alkyl sulfates, oxyethylenated or not, there can be cited in particular, sodium laurylsulfate, ammonium or triethanolamine laurylsulfate, monoethanolamine laurylsulfate, oxyethylenate sodium laurylether sulfate comprising, for example, 2.2 moles of ethylene oxide, oxyethylenated monoethanolamine laurylether sulfate comprising, for example, 2.2 moles of ethylene oxide.

These sulfates are generally used in concentrations (before dilution) of 0.5 to 15% and preferably 1 to 10% by weight.

By mixing with hydrogen peroxide, in dilution ratios most often used (from 1 to 3 times), finally to have amounts of hydrogen peroxide and ammonia sufficient to obtain clearing, the dye or bleach supports in cream form give a cream and the supports in gelable liquid form give a gel.

The invention extends to dye compositions that contain the dye support of the invention in mixture with direct or oxidation dyes.

The invention also extends to dye or bleach compositions, offered in two parts to be mixed at the time of use, the first part being made up of the support, possibly containing an oxidation dye, and the second part being made up of an oxidizing agent such as hydrogen peroxide, these two parts being put together in a packaging comprising their mode of use.

It is known that oxidation dyes are aromatic compounds of the diamine, aminophenol or phenol type. These compounds are generally not dyes in themselves but are transformed into dyes by condensation in the presence of an oxidizing medium generally made up of hydrogen peroxide. Of these oxidation dyes there are distinguished, on the one hand, bases that are known are para or ortho derivatives selected from diamines, aminophenols and, on the other hand, compound called modifiers or couplers that are known as meta derivatives and selected from meta-diamines, m-aminophenols, polyphenols.

Other dyes that can be used are direct dyes such as nitro dyes, anthraquinone, triphenylmethane, azo, metalliferous, xanthen, acridine, etc. derivatives.

Generally the dye supports of the invention contain from 0.5 to 10% by weight and preferably 1 to 3% by weight of quaternized polymers as defined above.

The pH of the supports of the invention is generally between 6 and 11 (and preferably 8 and 11), and is obtained by addition, if necessary, of a suitable basic agent, or an acid agent such as tartaric acid, citric, acetic, hydrochloric, phosphoric acid, etc.

Preferably, the compositions of the invention are free of anionic polymer.

This invention also has for its object a process of dyeing or bleaching hair, wherein principally there is applied to the hair a dye or bleach support as defined above, possibly containing dyes, and possibly mixed with an oxidizing agent such as hydrogen peroxide, the applied composition is allowed to act for a sufficient time to obtain the desired dyeing or bleaching effect, then the hair is rinsed.

Generally the composition is allowed to act for 5 to 45 minutes, and preferably for 15 to 30 minutes.

The amounts of dye or bleach composition applied to the hair are generally between about 10 and 100 g.

The compositions of this application can also be offered in the form of permanent compositions.

It is known that the standard technique for giving a permanent waving to the hair consists, in a first stage, in making an opening of the S—S bonds of the hair keratin with a composition containing a reducing agent, then, preferably after having rinsed the hair, reconstituting in a second stage said S—S bonds by applying to the hair, subjected to an extension, an oxidizing composition to give the desired shape to the hair.

The formulation of said reducing and oxidizing compositions is known and described in cosmetology works, particularly, by E. Sidi and C. Zviak, "Problemes Capillaires," Paris, 1966 (Gauthier-Villard).

The permanent compositions of the present application are preferably reducing compositions for the first stage of the permanent. The polymer I may also be incorporated in the oxidizing composition for the second stage.

Besides the reducing agent, these compositions contain adjuvants making it possible to offer them in lotion form or in powder form to be diluted in water.

Most often the reducing agent is a mercaptan such as, for example, thioglycerol or again a thioglycolic acid or its derivatives.

The compositions most often used have a base of thioglycolic acid or its derivatives, particularly its salts (ammonium, morpholine or ethylamine salt), its esters (glycol or glycerol ester), its hydrazide or its amide.

The concentration of the reducing agent is the concentration necessary to obtain the reduction of a sufficient number of S—S bonds. These concentrations have been studied and described in cosmetology works. For example, for thioglycolic acid, the concentration is generally on the order of about 1 to 11%.

The pH of these compositions for a first stage of a permanent generally varies from 7 to 10.

The reducing compositions preferably contain from 0.1 to 10% by weight of polymer of formula I, and preferably 0.25 to 5%.

These lotions for the first stage of the permanent are most often aqueous solutions that can further contain pH modifiers (for example, ammonium carbonate or bicarbonate), auxiliary reducing agents such as sulfites (for example, of sodium or potassium), solvents such as ethanol or isopropanol, nonionic or cationic surfactants, perfumes and/or dyes.

The polymers of formula I are compatible with the ingredients and adjuvants used in the permanent (or dye) compositions.

The invention also has for its object a process of giving a permanent to the hair, wherein there is applied to the hair a sufficient amount of a reducing composition as defined above, which is allowed to act for about 5 to 20 minutes, the hair is rinsed, and there is applied to the hair, subjected to an extension, an oxidizing composition in sufficient amount to reform the S-S bonds of the keratin of the hair.

The oxidizing agent is particularly hydrogen peroxide ($H_2O_2$), a presalt such as sodium perborate or persulfate, a bromate (of sodium, calcium, or magnesium), sodium iodate, etc.

Extension of the hair is generally done by rolling up in curlers, preferably done before application of the reducing composition.

After application of the oxidizing composition for a sufficient time, extension of the hair is stopped, then the hair is rinsed. Then it is set.

The compositions of this invention can also be lotions to be applied before or after a permanent. Besides water, these lotions can contain solvents (for example, ethanol or isopropanol), nonionic or cationic surfactants, pH modifiers, perfumes and/or dyes. They generally contain from 0.1 to 10% and preferably 0.25 to 5% by weight of the polymer of formula I. The invention also has for its object a process of treating hair which consists in applying to the hair, before or after a permanent, a sufficient amount of such a pre- or post-permanent lotion.

In the compositions of the invention, the polymers of formula I protect the hair from the degradation effects produced by dyeing, bleaching or a permanent. These degradation effects are well known.

Preferably the compositions of this invention do not contain anionic polymer.

When applied in the form of the compositions of the invention, the polymers of formula I facilitate untangling of wet and dry hair. They give the hair life shine and a soft touch.

Further, they prevent or reduce the development of static electricity in the hair.

The invention also has for its object certain polymers of formula I that are new products, and particularly polymers $P_2$ to $P_{14}$.

The following examples illustrate the invention without, however, limiting it.

EXAMPLE 1—DYE COMPOSITIONS

The dye support has the formula:

| | |
|---|---|
| Cetyl stearyl alcohol | 22 g |
| Oleic diethanolamide | 5 g |
| Sodium cetyl stearyl sulfate | 4 g |
| Polymer $P_1$ | 5 g |
| Ammonia at 22° Be | 12 ml |

To obtain the dye composition there are added to the support the following oxidation dyes and adjuvants:

| | |
|---|---|
| m-diaminoanisole sulfate | 0.048 g |
| Resorcin | 0.420 g |
| m-aminophenol | 0.150 g |
| nitro p-phenylene diamine | 0.085 g |
| p-toluylenediamine | 0.004 g |
| Trilon B (ethylenediaminetetraacetic acid) | 1.000 g |
| Sodium bisulfite d = 1.32 | 1.200 g |
| Water sufficient for | 100 g |

There are mixed 30 g of this formula with 45 g of 20-volume hydrogen peroxide; a smooth, consistent cream, pleasant to apply and adhering well to the hair is obtained.

After it has been on for 30 minutes, the hair is rinsed and dried.

Untangling of wet and dry hair is easy.

The hair has shine and body (volume) and is pleasant and silky to touch.

A blond shade is obtained with 100% white hair.

EXAMPLE 2—DYE COMPOSITION

The dye support has the formula:

| | |
|---|---|
| Stearyl alcohol | 20 g |
| Coco monoethanolamide | 5 g |
| Ammonium lauryl sulfate (20% fatty alcohols) | 10 g |
| Polymer $P_2$ | 6 g |
| Ammonia at 22° Be | 10 ml |

To obtain the dye composition the following oxidation dyes and adjuvants are added to this dye support:

| | |
|---|---|
| m-diaminosanisole sulfate | 0.048 g |
| Resorcin | 0.420 g |
| m-aminophenol | 0.150 g |
| nitro p-phenylene diamine | 0.085 g |
| p-toluylenediamine | 0.004 g |
| Trilon B (ethyelenediaminetetraacetic acid) | 1.000 g |
| Sodium bisulfite d = 1.32 | 1.200 g |
| Water sufficient for | 100 g |

There are mixed 30 g of this formula with 45 g of 20-volume hydrogen peroxide; a smooth, consistent cream, pleasant to apply and adhering well to the hair, is obtained.

After 30 minutes, the hair is rinsed and dried.

Untangling of wet and dry hair is easy.

The hair has shine, body (volume) and a pleasant, silky touch.

A blond shade is obtained with 100% white hair.

Comparable results were obtained by replacing polymer $P_2$ with an equivalent amount of polymer $P_3$ or $P_4$ or a mixture of $P_3$ and $P_4$.

EXAMPLE 3—DYE COMPOSITION

The dye support has the formula:

| | |
|---|---|
| Triethanolamine lauryl sulfate (40% MA) | 3 g |
| 2-octyl dodecanol sold under the name EUTANOL G by the Henkel company | |
| Oleic diethanolamide | 6 g |
| Oleo cetyl alcohol with 30 moles ethylene oxide sold under the name MERGITAL OC 30 by the Henkel company | 3 g |
| Oleic acid | 19 g |
| Polymer $P_4$ | 4 g |
| Butyl "Cellosolve" | 7 g |
| 96% ethyl alcohol | 8.5 g |
| Propylene glycol | 6 g |
| Ammonia at 22° Be | 20 ml |

To obtain the dye composition the following oxidation dyes and adjuvants are added to this support:

| | |
|---|---|
| p-aminophenol | 0.22 g |
| m-diaminoanisole sulfate | 0.044 g |
| Resorcin | 0.12 g |
| m-aminophenol | 0.075 g |
| Nitro p-phenylene diamine | 0.030 g |
| p-toluylene diamine | 0.16 g |
| Trilon B | 3 g |
| Sodium bisulfate d = 1.32 | 1.2 g |
| Water sufficient for | 100 g |

There are mixed in a bowl 30 g of this formula with 30 g of 20-volume hydrogen peroxide. A gel is obtained. It is applied by brush. It is allowed to stand for 30 to 40 minutes then rinsed.

The hair easily untangled. The touch is silky.

The hair is put up and dried.

The hair has shine, life and body (volume); the touch is silky and untangling is easy.

A light copperish blond shade is obtained on 100% white hair.

Comparable results were obtained by replacing the polymer $P_4$ with an equivalent amount of polymer $P_2$ or $P_5$ or by an equivalent amount of a mixture of polymers $P_2$ and $P_3$, or a mixture of $P_{12}$ and $P_{14}$.

EXAMPLE 4—DYE COMPOSITION

The dye support has the formula:

| | |
|---|---|
| EUTANOL G | 12 g |

-continued

| | | |
|---|---|---|
| Oleic diethanolamide | 9 | g |
| MERGITAL OC 30 | 2 | g |
| Oleic acid | 20 | g |
| Polymer P₂ | 3 | g |
| Butyl "Cellosolve" | 6 | g |
| 96% ethyl alcohol | 10 | g |
| Propylene glycol | 5 | g |
| Ammonia at 22° Be | 18 | ml |

To obtain the dye composition the following oxidation dyes and adjuvants are added to this support:

| | | |
|---|---|---|
| p-aminophenol | 0.08 | g |
| m-diaminoanisole sulfate | 0.04 | g |
| Resorcin | 0.248 | g |
| m-aminophenol | 0.07 | g |
| Nitro p-phenylenediamine | 0.002 | g |
| p-toluylene diamine | 0.3 | g |
| TRILON B | 3 | g |
| Sodium bisulfate d = 1.32 | 1.2 | g |
| Water sufficient for | 100 | g |

There are mixed in a bowl 30 g of this formula with 30 g of 20-volume hydrogen peroxide. A gel is obtained.

It is applied with a brush. It is allowed to stay for 30 to 40 minutes, and rinsed.

The hair untangles easily. The touch is silky.

It is put up and dried.

The hair has shine, life and body; the touch is silky and untangling is easy.

An ash blond shade is obtained on 100% white hair.

Comparable results were obtained by replacing polymer P₂ with an equivalent amount of P₄, P₅, P₇ or P₈.

EXAMPLE 5—DYE COMPOSITION

The dye support has the formula:

| | | |
|---|---|---|
| EUTANOL G | 12 | g |
| Oleic diethanolamide | 9 | g |
| MERGITAL OC 30 | 2 | g |
| Oleic acid | 20 | g |
| Polymer P₃ | 3 | g |
| Butyl "Cellosolve" | 6 | g |
| 96% ethyl alcohol | 10 | g |
| Propylene glycol | 5 | g |
| Ammonia at 22° Be | 18 | ml |

To obtain the dye composition the following oxidation dyes and adjuvants are added to this support:

| | | |
|---|---|---|
| 4-β-methoxyethylamino aniline dihydrochloride | 0.4 | g |
| p-aminophenol | 0.25 | g |
| Resorcin | 0.07 | g |
| m-aminophenol | 0.04 | g |
| N(β-hydroexyethyl) 5-amino 2-methyl phenol | 0.12 | g |
| (2,4-diamino) phenoxy ethanol dihydrochloride | 0.03 | g |
| Hydroquinone | 0.1 | g |
| Trilon B | 0.24 | g |
| Sodium bisulfate d = 1.32 | 1 | ml |
| Water sufficient for | 100 | g |

There are mixed in a bowl 30 g of this formula with 30 g of 20-volume hydrogen peroxide. A gel is obtained.

It is applied with a brush. It is allowed to stay for 30 to 40 minutes and rinsed.

The hair easily untangles and the touch is silky. It is put up and dried. The hair has shine, life and body. In the dry stage the touch is still silky and untangling is easy.

A light blond shade is obtained on 100% white hair.

Comparable results were obtained by replacing polymer P₃ with an equivalent amount of polymer P₂, P₄, P₁₁ or P₁₃.

EXAMPLE 6—BLEACH COMPOSITION

This composition has the formula:

| | | |
|---|---|---|
| Oleic acid | 20 | g |
| Monoethanolamine | 7 | g |
| Oleic alcohol | 12 | g |
| Triethanolamine lauryl sulfate with 40% active substance | 3 | g |
| MERGITAL OC 30 | 3 | g |
| Lauric diethanolamide | 12 | g |
| Polymer P₅ | 3 | g |
| Butylglycol | 5 | g |
| Ethyl alcohol | 8.5 | g |
| Propylene glycol | 6 | g |
| Trilon B | 0.2 | g |
| Ammonia at 22° Be | 18 | ml |
| Water sufficient for | 100 | g |

There are mixed in a bowl, before use, 60 g of this formula with 120 g of 20-volume hydrogen peroxide. A gelled liquid is obtained that is pleasant to apply and adheres well to hair by brush application. It is allowed to stay for 30 to 45 minutes and then rinsed.

The wet hair untangles easily, the touch is silky.

After drying, it has shine, life and body; the touch is silky and untangling is easy.

The hair is in a much better state than after bleaching with the same formula, even without the cationic polymer.

A dark blond shade is obtained on dark brown hair after bleaching.

Comparable results were obtained by replacing polymer P₅ with an equivalent amount of one of polymers P₂, P₃, P₄, P₆, P₈, P₉ or P₁₀.

A mode of preparing the cation polymers used in the embodiments of the composition is given below.

Preparation No 1

Preparation of polymer P₅ having groups of the formula:

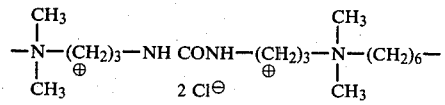

There are heated with reflux for 3 hours with vigorous agitation 46 g (0.2 mole) of N,N'-bis-(3-dimethylamine propyl) urea, 31 g (0.2 mole) of 1,6-dichlorohexane and 50 g of water. It is allowed to cool then 140 g of water are added to the resulting viscous solution. About 150 g of water are distilled to eliminate traces of residual 1,6-dichlorohexane, then the concentration of the solution is adjusted to 50% of the resulting polymer.

Analysis on Calculated Cl⊖: 9.22% 50% solution: Found: Cl⊖: 8.68%

Appearance: colorless, limpid, viscous solution.

Preparation No 2

Preparation of polymer P₂ having groups of the formula:

$$-\underset{\underset{CH_3\oplus}{|}}{\overset{\overset{CH_3}{|}}{N}}-(CH_2)_3-NH\ CONH-(CH_2)_3-\underset{\underset{CH_3\oplus}{|}}{\overset{\overset{CH_3}{|}}{N}}-CH_2-CHOH-CH_2-$$
$$2\ Cl^\ominus$$

The same mode of operation is used as in preparation No 1 with N,N'-bis-(3-dimethylamine propyl) urea and 1,3-dichloro-2-propanol.

Analysis on Calculated $Cl^\ominus$: 9.89% 50% solution: Found $Cl^\ominus$: 8.78%

Appearance: colorless, limpid, viscous solution.

Preparation No 3

Preparation of polymer $P_4$ having groups of formula:

$$-\underset{\underset{CH_3\oplus}{|}}{\overset{\overset{CH_3}{|}}{N}}-(CH_2)_3-NH\ CONH-(CH_2)_3-\underset{\underset{CH_3}{|}}{\overset{\overset{CH_3}{|}}{\overset{\oplus}{N}}}-CH_2CH=CH-CH_2-$$
$$2\ Br^\ominus$$

This compound is obtained by the same mode of operation as polymer $P_5$ from N,N'-bis-(3-dimethylaminopropyl) urea and trans-1-dibromo-2-butene.

Analysis on Calculated $Br^\ominus$: 18% 50% solution: Found $Br^\ominus$: 17.32%

Appearance: limpid, slightly yellow, viscous solution.

Preparation No 4

Preparation of polymer $P_3$ having groups of the formula:

$$-\underset{\underset{CH_3}{|}}{\overset{\overset{CH_3}{|}}{\overset{\oplus}{N}}}-(CH_2)_3-NH\ CONH-(CH_2)_3-\underset{\underset{CH_3\oplus}{|}}{\overset{\overset{CH_3}{|}}{N}}-CH_2-C_6H_4-CH_2-$$
$$2\ Br^\ominus$$

In a 500-cc Erlenmeyer flask are heated with reflux for 3 hours with vigorous agitation 46 g (0.2 mole) of N,N'-bis(3-dimenthylaminopropyl) urea, 52.8 g (0.2 mole) of 1,4-bis-(bromomethyl)benzene and 216 g of methanol. It is allowed to cool then the methol is distilled under reduced pressure. There are added 200 cc of water and the aqueous phase is washed three times with 100 cc of chloroform.

There are distilled under reduced pressure 150 cc of water and the concentration of the resulting solution is adjusted to 50% active substance by dilution with water.

Analysis on Calculated $Br^\ominus$: 16.2% 50% solution: Found $Br^\ominus$: 14.7%

Appearance: colorless, limpid, viscous solution.

Preparation No 5

Preparation of polymer $P_1$ having groups of the formula:

$$-\underset{\underset{CH_3\oplus}{|}}{\overset{\overset{CH_3}{|}}{N}}-(CH_2)_3-NH-CO-NH-(CH_2)_3-\underset{\underset{CH_3}{|}}{\overset{\overset{CH_3}{|}}{\overset{\oplus}{N}}}-CH_2CH_2-O-CH_2CH_2-$$
$$Cl^\ominus \qquad\qquad\qquad Cl^\ominus$$

There are mixed 46 g (0.2 mole) of N,N'-bis-(3-dimethylaminopropyl) urea and 50 g of water. It is heated to about 50°-60° C., 28.6 g (0.2 mole) of β,β'-dichloroethyl ether are introduced and heated with reflux for 11 hours. Then 140 cc of water are added. The water is distilled under a 50% solution of active substance is obtained.

Analysis on: Calculated $Cl^\ominus$: 9.5% 50% solution: Found $Cl^\ominus$: 9.19%

EXAMPLE 7—PERMANENT COMPOSITION

| (a) Reducing composition (first stage) | |
|---|---|
| Thioglycolic acid | 8 g |
| Ammonia sufficient for pH 7 | |
| Ammonium bicarbonate | 6.4 g |
| Dimethyl distearyl ammonium chloride | 0.2 g |
| Polymer $P_1$ | 3 g |
| Oleic acid oxyethylenated with 20 moles of ethylene oxide | 1 g |
| Perfume sufficient amount | |
| Water sufficient for | 100 g |
| (b) Fixer (2nd stage) | |
| Dimethyl stearyl ammonium chloride | 0.3 g |
| Phenacetin | 0.1 g |
| Citric acid | 0.3 g |
| Nonylphenol oxyethylenated with 9 moles of ethylene oxide | 1 g |
| $H_2O_2$ 8 volumes sufficient amount | |
| Dye, sufficient amount | |
| Perfume, sufficient amount | |
| Water, sufficient for | 100 g |

The reducing composition is applied to hair put up in curlers and allowed to say for 5 L to 15 minutes. It is carefully rinsed, then the fixer is applied and allowed to stay for 10 minutes. It is rinsed and the hair is put up.

Wet hair untangles easily. It is silky to the touch. After drying, the hair has shine and life, its touch is silky and untangling is easy. The hair does not develop static electricity.

Comparable results are obtained by replacing polymer $P_1$ with an equivalent amount of a mixture of polymers $P_6$ and $P_7$, or $P_9$ and $P_{11}$, or $P_{10}$ and $P_{13}$.

It is recalled that the 8-volume $H_2O_2$ solution is a solution able to release 8 times its volume of oxygen by decomposition according to the reaction $H_2O_2 \to H_2O + \frac{1}{2}O_2$.

Preparations

By operating in a manner similar to that described in the above examples of preparation, the following polymers are prepared whose formula was given above Polymer $P_6$: chloride content: 98% of theory
Polymer $P_7$: chloride content: 98% of theory
Polymer $P_8$: chloride content: 91% of theory Further, by causing the reaction, in the same mode of operation, of mixture of dihalides and diamines (equimolecular proportions of dihalides and diamines), and by using the following dihalides and diamines:

$$\underset{\underset{CH_3}{|}}{\overset{\overset{CH_3}{|}}{N}}-(CH_2)_3-NH-\overset{\overset{O}{\|}}{C}-NH-(CH_2)_3-\underset{\underset{CH_3}{|}}{\overset{\overset{CH_3}{|}}{N}} \qquad D_1$$

$$\underset{\underset{CH_3}{|}}{\overset{\overset{CH_3}{|}}{N}}-(CH_2)_3-\underset{\underset{CH_3}{|}}{\overset{\overset{CH_3}{|}}{N}} \qquad D_2$$

$$ClCH_2-CH_2O\ CH_2-CH_2\ Cl \qquad D_3$$

$$Cl-(CH_2)_6-Cl \qquad D_4$$

The following copolymers were prepared:

| Polymer | Quaternary Polymers Prepared from (moles) | Chloride Content (% of theory) |
|---|---|---|
| $P_9$ | $(\frac{3}{4})D_1 + (\frac{1}{4})D_2 + (\frac{3}{4})D_3 + (\frac{1}{4})D_4$ | 99% |
| $P_{10}$ | $(\frac{1}{4})D_1 + (\frac{3}{4})D_2 + (\frac{3}{4})D_3 + (\frac{1}{4})D_4$ | 100% |
| $P_{11}$ | $(\frac{1}{4})D_1 + (\frac{3}{4})D_2 + (\frac{1}{4})D_3 + (\frac{3}{4})D_4$ | 95% |
| $P_{12}$ | $(\frac{3}{4})D_1 + (\frac{1}{4})D_2 + (1)D_3$ | 100% |
| $P_{13}$ | $(\frac{1}{4})D_1 + (\frac{3}{4})D_2 + (1)D_3$ | 100% |
| $P_{14}$ | $(\frac{1}{2})D_1 + (\frac{1}{2})D_2 + (1)D_3$ | 99% |

According to a procedure analogous to that of EXAMPLE 7, permanent waving operations were performed with the compositions of the following Examples.

EXAMPLE 8

| (a) Reducing composition | |
|---|---|
| Ammonium thiolactate | 5 g |
| Monoethanolamine | 1,2 g |
| Sequestering agent | 0,2 g |
| polymer $P_1$ | 2 g |
| Oleic alcohol oxyethylenated with 20 moles of ethylene oxide | 1 g |
| perfume | 0,4 g |
| Water q.s.p. | 100 g |
| (b) oxidative composition | |
| dimethyldistearyl ammonium chloride | 0,3 g |
| phenacetin | 0,1 g |
| citric acid | 0,3 g |
| nonylphenol oxyethylenated with 9 moles of ethylene oxide | 1 g |
| hydrogen peroxide q.s.p. | 8 volumes |
| coloring agent q.s. (q.s. means: quantity sufficient) | |
| Water q.s.p. | 100 g |

EXAMPLE 9

| (a) reducing composition: | |
|---|---|
| ammonium sulfite | 4 g |
| ammonium bisulfite | 3 g |
| monoethanolamine | 2 g |
| diethanolamine | 2 g |
| polymer $P_1$ | 1,5 g |
| Nonylphenol oxyethylenated with 9 moles of ethylene oxide | 0,5 g |
| perfume | 0,4 g |
| Water q.s.p. | 100 g |
| (b) oxidative composition | |
| dimethyldistearyl ammonium chloride | 0,3 g |
| phenacetine | 0,1 g |
| citric acid | 0,3 g |
| nonylphenol oxyethylenated with 9 moles of ethylene oxide | 1 g |
| hydrogen peroxide q.s.p. | 8 volumes |
| coloring agent, q.s. | |
| perfume q.s | |
| Water q.s.p. | 100 g |

Similar results were obtained by replacing polymer $P_1$ in the reducing composition by an equivalent amount of polymer $P_2$, $P_3$, $P_4$, $P_5$, $P_8$ or $P_{12}$.

EXAMPLE 10

| (a) reducing composition: | |
|---|---|
| thioglycolic acid | 8 g |
| ammonia, q.s.p. | pH = 7 |
| ammonium bicarbonate | 6,4 g |
| dimethyldistearyl ammonium chloride | 0,2 g |
| oleic alcohol oxyethylenated with 20 moles of ethylene oxide | 1 g |
| Perfume, q.s. | |

| Water, q.s.p. | 100 g |
|---|---|
| (b) oxidative composition | |
| phenacetin | 0,1 g |
| dimethyldistearyl ammonium chloride | 0,2 g |
| citric acid | 0,3 g |
| nonylphenol oxyethylenated with 9 moles of ethylene oxide | 1 g |
| hydrogen peroxide, q.s.p. | 8 volumes |
| polymer $P_1$ | 1,5 g |
| coloring agent | 0,2 g |
| perfume | 0,3 g |
| Water, q.s.p. | 100 g |

Polymer $P_1$ may be replaced, in the oxidative composition, by an equivalent amount of polymer $P_2$, $P_3$, or $P_4$.

We claim:

1. A hair dye composition free of an anionic polymer comprising an oxidation hair dye present in an amount effective to dye hair and a dye support therefor, said dye support comprising at least one polymer having units of the formula

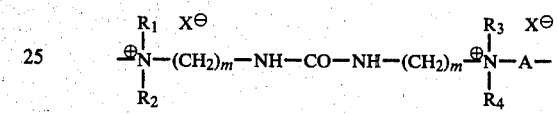

wherein $R_1$, $R_2$, $R_3$ and $R_4$, each independently represent alkyl having 1-20 carbon atoms, hydroxyalkyl having 1-20 carbon atoms, cycloalkyl having 5 or 6 carbon atoms in the ring, alkyl substituted cycloalkyl having 5 or 6 carbon atoms in the ring and wherein the total number of carbon atoms is less than 20 and phenylalkyl wherein the alkyl moiety has 1-3 carbon atoms, or one or both of the pairs $R_1$ and $R_2$, and $R_3$ and $R_4$, together with the nitrogen atom to which each of said respective pairs is attached, form a ring having 2-6 carbon atoms or a ring having 2-6 carbon atoms and a heteroatom other than nitrogen;

$X^\ominus$ is an inorganic or organic acid anion;

m is 2 or 3; and

A represents linear or branched alkylene or alkenylene having 2-18 carbon atoms, linear or branched alkylene or alkenylene having 2-18 carbon atoms and substituted by one or more of —OH or =O groups, or linear or branched alkylene or alkenylene having 2-18 carbon atoms and interrupted by one or more of oxygen, sulfur, nitrogen or phenylene groups.

2. The hair dye composition of claim 1 wherein the heteroatom in the ring formed by one or both pairs of $R_1$ and $R_2$, and $R_3$ and $R_4$ together with the nitrogen atom to which each of said respective pairs is attached is oxygen or sulfur.

3. The hair dye composition of claim 1 wherein A represents ortho xylylene, meta xylylene, para xylylene, $-(CH_2)_n-S-(CH_2)_n-$, $-(CH_2)_n-O-(CH_2)_n-$, $-(CH_2)_n-S-S-(CH_2)_n-$, $-(CH_2)_n-SO-(CH_2)_n-$, $-(CH_2)_n-SO_2-(CH_2)_n-$, $-CH_2-CO-CH_2-$, $-CH_2-C_6H_4-C_6H_4-CH_2-$, $-CH_2-C_6H_4-O-C_6H_4-CH_2-$, $-CH_2-C_4H_4-SO_2-C_6H_4-CH_2-$, $-C_6H_4-CH_2-C_6H_4-$, $-C_6H_4-C(CH_3)_2-C_6H_4-$, $-C_6H_4-CHOH-C_6H_4-$, $-C_6H_4-CO-C_6H_4-$, —alkylene—N($R_5$)—alkylene—, or arylene—$X_1$—arylene—, wherein $X_1$ represents —O—, —S—, —S—S—, —SO—, —$SO_2$— or —N($R_5$)—, $R_5$ represents alkyl, cycloalkyl or aralkyl, having up to 20 carbon atoms, said alkylene and arylene groups having up to 20 carbon atoms and n is 2 or 3, and $X^\ominus$ is a halide or an anion derived from a phosphoric acid, sulfuric acid, paratoluene sulfonic acid or a carboxylic acid.

4. The hair dye composition of claim 1 wherein said polymer has a molecular weight between 1,500 and 50,000.

5. The hair dye composition of claim 1 wherein A represents $-(CH_2)_n-O-(CH_2)_n-$ wherein n is 2 or 3, $-CH_2-C_6H_4-CH_2-$, $-CH_2-CHOH-CH_2-$, $-(CH_2)_p-$ wherein p is 2 to 18 or $-(CH_2)_{n_1}-CH=CH-(CH_2)_{n_2}-$ wherein $n_1$ and $n_2$ are integers including zero, the sum of $n_1$ and $n_2$ being at most 16.

6. The hair dye composition of claim 1 which also includes an effective amount of an adjuvant to provide said composition in the form of a cream, said adjuvant being a $C_{12}$-$C_{20}$ fatty acid soap or a natural or synthetic $C_{12}$-$C_{20}$ fatty alcohol in the presence of a nonionic emulsifier.

7. The hair dye composition of claim 1 which also includes an effective amount of an adjuvant to provide said composition in the form of a gelable liquid which on admixture with hydrogen peroxide gives a gel, said adjuvant being (a) a mixture of an oxyethylenated or polyglycerolated nonionic compound and a solvent or (b) a mixture of a liquid fatty acid soap and a solvent.

8. The hair dye composition of claim 7 which also includes one or more of a fatty amide, a natural or synthetic fatty alcohol, a natural or synthetic oxyethylenated fatty alcohol, a preservative agent, a sequestering agent or a perfume.

9. The composition of claim 6 or claim 7 wherein said polymer is present in an amount from 0.5 to 10 percent by weight.

10. The composition of claim 6 or claim 7 wherein said polymer is present in an amount from 1 to 3 percent by weight.

11. A two-part hair dye composition, said two parts to be mixed together at the time of use, one part comprising the composition of claim 6 or claim 7, the other part being an oxidizing agent.

12. The two-part hair dye composition of claim 11 wherein said oxidizing agent is hydrogen peroxide.

13. A hair dye composition free of an anionic polymer comprising an oxidation hair dye present in an amount effective to dye hair and a dye support therefor, said dye support comprising at least one polymer having the units of the formula

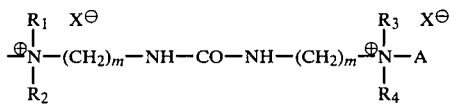

wherein
$R_1=R_2=R_3=R_4=CH_3$ or $C_2H_5$;
$X=Cl$
$m=3$; and
when $R_1-R_4=CH_3$, A represents $-CH_2CH_2O-CH_2CH_2-$, $-CH_2-C_6H_4-CH_2-$, $-CH_2-CHOH-CH_2-$, $-(CH_2)_6-$ or $-CH_2-CH=CH-CH_2-$, and
when $R_1-R_4=C_2H_5$, A represents $-(CH_2)_6-$, $-CH_2-CHOH-CH_2-$ or $-CH_2-CH=CH-CH_2-$.

14. The hair dye composition of claim 13 wherein $R_1=R_2=R_3=R_4=CH_3$, $m=3$, $X=Cl$ and A represents $-CH_2CH_2-O-CH_2-CH_2-$.

15. The hair dye composition of claim 13 wherein $R_1=R_2=R_3=R_4=CH_3$, $m=3$, $X=Cl$ and A represents $-CH_2-CHOH-CH_2-$.

16. The hair dye composition of claim 13 wherein $R_1=R_2=R_3=R_4=CH_3$, $m=3$, $X=Cl$ and A represents $-CH_2-C_6H_4-CH_2-$.

17. The hair dye composition of claim 13 wherein $R_1=R_2=R_3=R_4=CH_3$, $m=3$, $X=Cl$ and A represents $-CH_2-CH=CH-CH_2-$.

18. The hair dye composition of claim 13 wherein $R_1=R_2=R_3=R_4=CH_3$, $m=3$, $X=Cl$ and A represents $-(CH_2)_6-$.

19. The hair dye composition of claim 13 wherein $R_1=R_2=R_3=R_4=C_2H_5$, $m=3$, $X=Cl$ and A represents $-(CH_2)_6-$.

20. The hair dye composition of claim 13 wherein $R_1=R_2=R_3=R_4=C_2H_5$, $m=3$, $X=Cl$ and A represents $-CH_2-CHOH-CH_2-$.

21. The hair dye composition of claim 13 wherein $R_1=R_2=R_3=R_4=C_2H_5$, $m=3$, $X=Cl$ and A represents $-CH_2-CH=CH-CH_2-$.

22. A hair dye composition free from an anionic polymer in cream form comprising an oxidation hair dye present in an amount effective to dye hair, at least one polymer having units of the formula

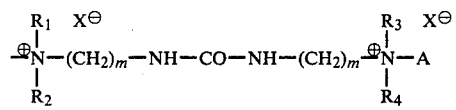

wherein
$R_1=R_2=R_3=R_4=CH_3$ or $C_2H_5$;
X is Cl;
m is 3; wherein
when $R_1-R_4=CH_3$, A represents $-CH_2-CH_2-O-CH_2-CH_2-$, $-CH_2-C_6H_4-CH_2-$, $-CH_2-CHOH-CH_2-$, $-(CH_2)_6-$ or $-CH_2-CH=CH-CH_2-$ and when $R_1-R_4=C_2H_5$, A represents $-(CH_2)_6-$, $-CH_2-CHOH-CH_2-$ or $-CH_2-CH=CH-CH_2-$; and at least one of a $C_{12}$ to $C_{20}$ fatty acid soap or a $C_{12}$ to $C_{20}$ fatty alcohol in the presence of a nonionic emulsifier.

23. The hair dye composition of claim 22 wherein the fatty acid of said soap is selected from the group consisting of lauric acid, myristic acid, palmitic acid, oleic acid stearic acid, hydroxy stearic acid, arachic acid, ricinoleic acid, lanolinic acid, phenylstearic acid, and linoleic acid.

24. The hair dye composition of claim 22 wherein said soap is made using an alkalizing agent selected from the group consisting of soda, potash, ammonia, monoethanolamine, diethanolamine, triethanolamine, monoisopropanolamine, diisopropanolamine, N-ethylmorpholine, 2-amino-1-butanol, 2-amino-2-methyl-1-propanol and mixtures thereof.

25. The hair dye composition of claim 22 wherein said soap is present in an amount between 1 and 60 percent by weight of said composition.

26. The hair dye composition of claim 22 wherein said soap is present in an amount between 5 and 30 percent by weight of said composition.

27. The hair dye composition of claim 22 wherein said $C_{12}$ to $C_{20}$ fatty alcohol is selected from the alcohols derived from copra fatty acids, myristic alcohol, cetyl alcohol, stearyl alcohol, arachidyl alcohol, isostearyl alcohol, hydroxystearyl alcohol, oleic alcohol and ricinoleic alcohol.

28. The hair dye composition of claim 22 wherein said $C_{12}$ to $C_{20}$ fatty alcohol is present in an amount between 1 and 60 percent by weight of said composition.

29. The hair dye composition of claim 22 wherein said $C_{12}$ to $C_{20}$ fatty alcohol is present in an amount between 5 and 30 percent by weight of said composition.

30. The hair dye composition of claim 22 wherein said nonionic emulsifier is an oxyethylenated or polyglycerolated natural or synthetic $C_{10}$–$C_{20}$ fatty alcohol present in an amount between 1 and 60 percent by weight of said composition.

31. The hair dye composition of claim 22 wherein said nonionic emulsifier is selected from the group consisting of oleic alcohol oxyethylenated with 10-30 moles of ethylene oxide, cetyl alcohol oxyethylenated with 6 to 10 moles of ethylene oxide, cetylstearyl alcohol oxyethylenated with 10 moles of ethylene oxide, oleocetyl alcohol oxyethylenated with 30 moles of ethylene oxide, stearyl alcohol oxyethylenated with 10, 15 or 20 moles of ethylene oxide, oleic alcohol polyglycerolated with 4 moles of glycerol and a $C_9$ to $C_{20}$ synthetic fatty alcohol oxyethylenated with 5 to 30 moles of ethylene oxide.

32. The hair dye composition of claim 30 wherein said nonionic emulsifier is present in an amount between 5 and 30 percent by weight of said composition.

33. A hair dye composition free from an anionic polymer in gelable liquid form comprising an oxidation hair dye present in an amount effective to dye hair, at least one polymer having units of the formula

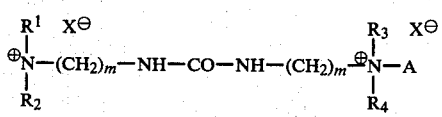

wherein
$R_1=R_2=R_3=R_4=CH_3$ or $C_2H_5$;
X is Cl;
m is 3; wherein
when $R_1$—$R_4=CH_3$, A represents —CH$_2$—CH$_2$—O—CH$_2$—CH$_2$—, —CH$_2$—C$_6$H$_4$—CH$_2$—, —CH$_2$—CHOH—CH$_2$—, —(CH$_2$)$_6$— or —CH$_2$—CH=CH—CH$_2$—, and when $R_1$—$R_4=C_2H_5$, A represents —(CH$_2$)$_6$—, —CH$_2$—CHOH—CH$_2$— or —CH$_2$—CH=CH—CH$_2$—; and
(a) a mixture of an oxyethylenated or polyglycerolated nonionic compound and a solvent or
(b) a mixture of a liquid fatty acid soap and a solvent.

34. The hair dye composition of claim 33 wherein said mixture (a) the nonionic compound is oleic alcohol oxyethylenated with 4 or 10 moles of ethylene oxide, a $C_{10}$-$C_{20}$ synthetic fatty alcohol oxyethylenated with 4 or 6 moles of ethylene oxide and a $C_9$-$C_{15}$ synthetic fatty alcohol oxyethylenated with 2, 6 or 9 moles of ethylene oxide.

35. The hair dye composition of claim 33 where in said mixture (a) the nonionic compound is nonylphenol polyether oxyethylenated with 4 or 9 moles of ethylene oxide.

36. The hair dye composition of claim 33 where said nonionic compound is present in an amount between 5 and 60 percent by weight of said composition.

37. The hair dye composition of claim 33 where said nonionic compound is present in an amount between 5 and 40 percent by weight of said composition.

38. The hair dye composition of claim 33 where in said mixture (a) the nonionic compound is selected from the group consisting of oleic alcohol polyglycerolated with 2 or 4 moles of glycerol.

39. The hair dye composition of claim 33 where in said mixture (b) the fatty acid soap is derived from (1) an acid selected from the group consisting of oleic acid, linoleic aicd, ricinoleic acid and isostearic acid and (2) an alkalizing agent selected from the group consisting of soda, potash, ammonia, monoethanolamine, diethanolamine, triethanolamine, mono-isopropanolamine, di-isopropanolamine, N-ethylmorpholine, 2-amino-1-butanol, 2-amino-2-methyl-1-propanol and mixtures thereof.

40. The hair dye composition of claim 33 wherein said fatty acid soap is present in an amount between 5 and 60 percent by weight of said composition.

41. The hair dye composition of claim 33 wherein said fatty acid soap is present in an amount between 5 and 40 percent by weight of said composition.

42. The composition of claim 33 where in mixture (a) or mixture (b) the solvent is selected from the group consisting of ethyl alcohol, propylalcohol, isopropyl alcohol, propylene glycol, methyl glycol, ethyl glycol, butyl glycol, diethylene glycol, dipropylene glycol, hexylene glycol and diethylene glycol monoethyl ether.

43. The composition of claim 42 wherein said solvent is present in an amount between 2 and 20 weight percent.

44. The composition of claim 42 wherein said solvent is present in an amount between 5 and 15 weight percent.

45. The composition of claim 33 which also includes a fatty amide selected from the group consisting of oleic diethanolamide, lauric diethanolamide, copra monoethanolamide and copra diethanolamide present in an amount between 0.5 and 15 percent by weight.

46. The composition of claim 33 which also includes a natural or synthetic alcohol selected from the group consisting of oleic alcohol, lauric alcohol, octyldodecyl alcohol, hexyldodecyl alcohol, isostearyl alcohol, ricinoleyl alcohol and linoleyl alcohol present in an amount of 1 to 25 percent by weight.

47. A process for dyeing hair comprising applying to said hair an effective amount of the composition of claim 6 or 7 to dye said hair, permitting said composition to remain in contact with the hair for a time sufficient to obtain the desired dyeing effect and rinsing said hair.

* * * * *